United States Patent [19]

Tuengler

[11] Patent Number: 5,789,262

[45] Date of Patent: Aug. 4, 1998

[54] NEPHELOMETRIC AND TURBIDIMETRIC PROTEIN DETERINATIONS FREE OF AN EXCESS OF ANTIGEN

[75] Inventor: Peter Tuengler, Marburg, Germany

[73] Assignee: Behring Diagnostics GmbH, Marburg, Germany

[21] Appl. No.: 674,818

[22] Filed: Jul. 3, 1996

[30] Foreign Application Priority Data

Jul. 5, 1995 [DE] Germany .................. 195 24 414.1

[51] Int. Cl.⁶ .................................. G01N 33/553
[52] U.S. Cl. .................. 436/534; 435/7.1; 435/7.92; 435/7.93; 435/7.94; 436/507; 436/517; 436/536; 436/539; 436/164; 436/179; 436/180; 436/805; 436/824; 422/73; 422/82.09
[58] Field of Search ............. 435/7.1, 7.2, 7.91, 435/7.92, 7.93, 7.94, 7.95, 534; 436/507, 510, 517, 536, 539, 164, 177, 178, 179, 180, 805, 824; 422/73, 82.09

[56] References Cited

U.S. PATENT DOCUMENTS

| | | | |
|---|---|---|---|
| 3,861,877 | 1/1975 | Matharani et al. | 23/230 B |
| 4,157,871 | 6/1979 | Anderson et al. | |
| 4,174,952 | 11/1979 | Cannell et al. | 23/230 B |
| 4,213,764 | 7/1980 | O'Connor | 23/230 B |
| 4,290,997 | 9/1981 | Suovaniemi | 422/73 |
| 4,434,236 | 2/1984 | Freytag | 436/512 |
| 4,457,893 | 7/1984 | Takekawa | 422/64 |
| 4,551,426 | 11/1985 | Freytag et al. | 435/7 |
| 4,636,479 | 1/1987 | Martin et al. | 436/533 |
| 4,847,199 | 7/1989 | Snyder et al. | 435/36 |
| 5,445,936 | 8/1995 | Piran et al. | 435/6 |

FOREIGN PATENT DOCUMENTS 33 47 162 A1  7/1985  Germany .

OTHER PUBLICATIONS

Williams et al., Methods in Immunology and Imunochemistry, pp. 86–102. Academic Press, 1971.

*Primary Examiner*—Christopher L. Chin
*Assistant Examiner*—Bao-Thuy L. Nguyen
*Attorney, Agent, or Firm*—Finnegan, Henderson, Farabow, Garrett & Dunner, L.L.P.

[57] ABSTRACT

The invention relates to the area of protein determinations in homogeneous solution by means of antigen-mediated precipitation by antibodies or using latex materials coated with antibodies and subsequent optical measurement of the precipitation reaction by a nephelometric or turbidimetric measurement.

15 Claims, No Drawings

NEPHELOMETRIC AND TURBIDIMETRIC PROTEIN DETERINATIONS FREE OF AN EXCESS OF ANTIGEN

The invention relates to the area of protein determinations in homogeneous solution by means of antigen-mediated precipitation by antibodies or using latex materials coated with antibodies and subsequent optical measurement of the precipitation reaction by a nephelometric or turbidimetric measurement.

As is evident from the well-known reaction plot of Heidelberger and Kendall for immunoprecipitation, such reactions may be ambiguous, i.e. after a maximum has been exceeded there is a decrease in the signal at high antigen concentrations, and the value of this cannot be differentiated in one measurement from the signal of a lower antigen concentration.

Since this problem of measurement with an excess of antigen represents a crucial limitation on the known nephelometric and turbidimetric measurement methods, a number of solutions has already been proposed. Thus, there are kinetic methods which establish the presence of an excess of antigen by analyzing the kinetics of reaction (1st derivative) and then institute an appropriate remeasurement (ANDERSON, U.S. 4,157,871) or permit unambiguous analysis of the plots by appropriate technical steps (DE-A-33 47 162).

Attempts have furthermore been made to solve the problem in the so-called "restart method" by subsequently adding a defined amount of a standard preparation of an analyte and recording the subsequent course of the reaction.

A disadvantage in principle of the kinetic methods is the fact that recording of measurements throughout the incubation time is necessary. This blocks the optical measurement system correspondingly during this time and permits only a small sample throughput. The analysis is also correspondingly memory-intensive. The restart method does not have this disadvantage but is, owing to the need for an appropriate well-defined standard, associated with higher test costs.

Thus the object of the present invention is a method of measurement which permits test schemes free of an excess of antigen without an increase in test costs and with high sample throughput.

This object is achieved essentially by providing the embodiments described in the claims.

The invention is based on the observation that a correct result is always obtained with samples with an extremely higher antigen concentration which correspondingly produce a signal which is too low by diluting the sample before addition to the test. Logically, as a rule, critical samples or samples with critical tests are investigated several times in different sample dilutions in automated equipment, and the results are subsequently manually checked for validity. However, this correspondingly reduces the sample throughput and increases the test costs per sample investigated.

It has now been found that the object on which the application is based can be achieved by initially subjecting an aliquot of the amount of sample (or of the sample dilution made before the test) to an incubation in the test with a complete reagent content and, after a certain reaction time, recording a measurement (or a measurement difference from the initial value in a fixed time measurement). Only then is the remainder of the sample (or sample dilution) added to the same reaction mixture, and then the latter is subjected to another incubation step and an analogous measurement.

The aliquot can be a ratio of 1–25%, preferably 2–20%, preferably 5–10%, of the total amount of sample.

In the case of a sample with such a high antigen concentration which causes an antigen excess effect in a conventional test, a clear measurement signal will be produced with the modified mixture mentioned in the preliminary reaction because of the distinctly smaller amount of sample, and can be rapidly, simply and reliably detected by the analysis equipment on the basis of a threshold examination. Samples which can also be analyzed without difficulty and correctly in the conventional test on the ascending branch of the Heidelberger-Kendall plot provide only a weak, or no, measurement signal in the preliminary reaction, i.e. the analysis equipment recognizes the normal case here due to the value being below the threshold.

In another advantageous embodiment, the analysis equipment can undertake a quantitative analysis without remeasurement even of extreme samples by producing two calibration plots for a test (for the preliminary reaction and the main reaction). As a rule, no quantification of the available measurement signal is undertaken with such samples, which do not, as a rule, occur too often; on the contrary remeasurements are undertaken until the main reaction can be quantified. In turn, the pure examination of the threshold in the preliminary reaction as a rule permits distinctly shorter incubation times than for the main reaction which is necessary to quantify the measurement signal, so that the possible test throughput on the analysis equipment is reduced only slightly (and not halved, for example).

The following examples serve to illustrate the invention.

EXAMPLE 1

Determination of albumin in urine

5 μL of a urine sample which has previously been diluted 1:5 with N diluent (order No. OUMT, Behringwerke AG) is introduced together with 55 μL of N reaction buffer (order No. OUMS, Behringwerke AG) into a reaction cuvette. The reaction is started by adding 40 μL of reagent (N antiserum against human albumin, order No. OSAL, Behringwerke AG) which is likewise introduced into the cuvette together with 100 μL of reaction buffer (order No. OUMS, Behringwerke AG). The mixture is thoroughly mixed and an initial signal is recorded; after exactly 2 minutes, another measurement is carried out, and the difference from the initial signal represents the signal from the preliminary reaction. After a further 4 minutes, the last measurement is carried out; the difference of this from the initial signal represents the signal from the main reaction.

The following signals are obtained with the Behring nephelometer II (Behringwerke AG, Marburg, Germany, order No. O VI A) for a calibration plot (the unit of measurement of the scattered light signals here is the bit):

|  | Signal from the preliminary reaction | | Signal from the main reaction | |
|---|---|---|---|---|
| Lower point on the calibration plot (dilution 1:10240) | 5 | bit | 768 | bit |
| Upper point on the calibration plot (dilution 1:640) | 566 | bit | 6255 | bit |
| Sample 1 (normal urine, 1:5) | 2 | bit | 35 | bit |
| Sample 2 (pathol. urine, 1:5) | 20 | bit | 1805 | bit |
| Sample 3 (serum, 1:5) | 4456 | bit | 1895 | bit |

Samples 1 and 2 show the typical behavior of samples which are below the measurement range, and in the measurement range. respectively of the test mixture. Sample 3 shows a distinct reaction in the preliminary reaction, resulting in a signal which is above that of the top point on the calibration plot. It is possible in this way to generate a flag which, for example, effects another measurement for quantification of the result with a higher sample dilution. In the classical mixture without a preliminary reaction, sample 3, which has an extremely high analyte concentration relative to the measurement range, generates a signal which is comparable to that of sample 2 or even sample 1. The classical measurement would therefore point to a false result which is too low.

EXAMPLE 2
Determination of IgM in serum

The procedure is analogous to the measurement in Example 1 with 50 µL of a serum sample previously diluted 1:20 (in N diluent), using as reagent 40 µL of N antiserum against human IgM (order No. OSAT, Behringwerke AG).

| Determination of IgM in serum | | | | |
|---|---|---|---|---|
| | Signal from the preliminary reaction | | Signal from the main reaction | |
| Lower point on the calibration plot (dilution 1:80) | 5 | bit | 60 | bit |
| Upper point on the calibration plot (dilution 1:2.5) | 460 | bit | 4494 | bit |
| Sample 1 (normal serum, 1:20) | 11 | bit | 700 | bit |
| Sample 2 (IgM myeloma, 1:20) | 4414 | bit | 5128 | bit |
| Ditto, remeasurement 1:100 | 864 | bit | 4368 | bit |
| Ditto, remeasurement 1:400 | 101 | bit | 2053 | bit |
| Sample 3 (IgM myeloma, 1:20) | 5438 | bit | >16384 | bit |
| Ditto, remeasurement 1:400 | 180 | bit | 2792 | bit |
| Sample 4 (IgM myeloma, 1:20) | 514 | bit | 4402 | bit |
| Ditto, remeasurement 1:100 | 43 | bit | 1421 | bit |

The facts here are the same as in Example 1. It is possible to quantify problem samples with an extremely high analyte concentration by successive dilution of the sample until the state is reached in which the value from the preliminary reaction is within or below that corresponding to the calibration plot and the measurement of the sample in the main reaction is located in the values predetermined in the calibration plot. Whereas IgM myeloma samples 2 and 3 would also have been correctly identified by the measurement range being exceeded in the main reaction, this is no longer the case for IgM myeloma 4. In this case, quantification takes place by the automatic redetermination as a consequence of the threshold being exceeded in the preliminary reaction.

I claim:

1. An immunochemical method for determining the concentration of an analyte in a sample of a biological material by an analyte-dependent precipitation reaction with analyte-specific binding partners, comprising:
  a) incubating the sample with a reagent which contains at least one analyte-specific binding partner, optionally bound to a particle,
  b) binding of the analyte to the analyte-specific binding partner,
  c) measuring the analyte-dependent precipitation reaction,
  d) determining the analyte concentration by conducting the measurement, with the sample being added in two steps:
    i) incubating an aliquot, preferably ⅕ to ¹/₁₀₀, of the sample with the reagent in a first reaction and measuring the analyte-dependent precipitation reaction;
    ii) incubating the remaining sample with the reaction mixture from step i) in a second reaction and measuring the analyte-dependent precipitation reaction,
  wherein the analyte concentration is calculated from the measurement taken in step d) ii) when the measurement of step d) i) is either equal to, above, or below a defined threshold.

2. The method as claimed in claim 1, where the analyte-specific binding partner is an antibody.

3. The method as claimed in claim 1, where the measurement of the analyte-dependent precipitation reaction takes place by means of turbidimetric measurement.

4. The method as claimed in claim 1, where the measurement of the analyte-dependent precipitation reaction takes place by means of nephelometric measurement.

5. The method as claimed in claim 1, where the measurement of the analyte-dependent precipitation reaction takes place by means of kinetic measurement.

6. The method as claimed in claim 1, where the measurement of the analyte-dependent precipitation reaction takes place by means of a fixed-time kinetic measurement.

7. The method as claimed in claim 1, where the measurement of the analyte-dependent precipitation reaction takes place by means of a fixed-value measurement.

8. The method as claimed in claim 1, where the measurement of the analyte-dependent precipitation reaction takes place by means of endpoint measurement.

9. The method as claimed in claim 1, where the analyte concentration is calculated from the measurement taken in step d) ii) when the measurement taken in step d) i) is below a defined threshold.

10. The method as claimed in claim 1, where the analyte concentration is calculated from the measurement taken in step d) ii) in a newly set-up analysis with reduced sample content when the measurement taken in step d) i) in the original mixture is above a defined threshold.

11. An immunochemical method for determining the concentration of an analyte in a sample of a biological material by an analyte-dependent precipitation reaction with analyte-specific binding partners, comprising:
  a) incubating the sample with a reagent which contains at least one analyte-specific binding partner, optionally bound to a particle,
  b) binding of the analyte to the analyte-specific binding partner,
  measuring the analyte-dependent precipitation reaction,
  d) determining the analyte concentration by conducting the measurement, with the sample being added in one step:
    i) incubating an aliquot, preferably ⅕ to ¹/₁₀₀, of the sample with the reagent in a reaction and measuring the analyte-dependent precipitation reaction,
  where the analyte concentration is calculated from the measurement taken in d) i) when the measurement of step d) i) is above a defined threshold.

12. The method as claimed in claim 1, where the sample is used undiluted.

13. The method as claimed in claim 1, where the sample undergoes preliminary dilution.

14. The method as claimed in claim 1, where the analysis takes place by comparing the measurements found with a calibration plot.

15. The method as claimed in claim 1, where the analysis takes place by comparison of two calibration plots, one of which has been recorded under the conditions of step d) i) and the second has been recorded under the conditions of step d) ii).

* * * * *